(12) United States Patent
Vortman et al.

(10) Patent No.: US 10,130,828 B2
(45) Date of Patent: Nov. 20, 2018

(54) CONTROLLED, NON-LINEAR FOCUSED ULTRASOUND TREATMENT

(75) Inventors: Kobi Vortman, Haifa (IL); Shuki Vitek, Haifa (IL); David Freundlich, Haifa (IL)

(73) Assignee: INSIGHTEC LTD., Tirat Carmel (IL)

( * ) Notice: Subject to any disclaimer, the term of this patent is extended or adjusted under 35 U.S.C. 154(b) by 2249 days.

(21) Appl. No.: 11/993,443

(22) PCT Filed: Jun. 19, 2006

(86) PCT No.: PCT/IB2006/001641
§ 371 (c)(1),
(2), (4) Date: Jun. 4, 2010

(87) PCT Pub. No.: WO2006/136912
PCT Pub. Date: Dec. 28, 2006

(65) Prior Publication Data
US 2010/0241036 A1    Sep. 23, 2010

Related U.S. Application Data

(63) Continuation-in-part of application No. 11/158,657, filed on Jun. 21, 2005, now abandoned.

(51) Int. Cl.
*A61H 1/00* (2006.01)
*A61N 7/02* (2006.01)
(Continued)

(52) U.S. Cl.
CPC ............... *A61N 7/02* (2013.01); *A61B 8/467* (2013.01); *A61B 8/481* (2013.01); *A61B 90/37* (2016.02);
(Continued)

(58) Field of Classification Search
CPC .... A61B 2017/22008; A61B 2090/374; A61B 2090/376; A61B 2090/378; A61B 8/467; A61B 8/481; A61B 90/37; A61N 7/02
(Continued)

(56) References Cited

U.S. PATENT DOCUMENTS 2,795,709 A    6/1957  Camp
3,142,035 A    7/1964  Harris
(Continued)

FOREIGN PATENT DOCUMENTS

DE    4345308 C2    2/2001
EP    0031614 A1    7/1981
(Continued)

OTHER PUBLICATIONS

Botros et al., "A hybrid computational model for ultrasound phased-array heating in presence of strongly scattering obstacles," IEEE Trans. On Biomed. Eng., vol. 44, No. 11, pp. 1039-1050 (Nov. 1997).
(Continued)

*Primary Examiner* — Amelie R Gillman
(74) *Attorney, Agent, or Firm* — Morgan, Lewis & Bockius LLP (57) ABSTRACT

A system (10) for treating tissue within a body is configured to deliver a first level of ultrasound energy to a target tissue region (42) for a first duration resulting in the generation of micro-bubbles (56) in the target tissue region, determine one or more characteristics of the target tissue region in the presence of the micro-bubbles, and deliver a second level of ultrasound energy to the target tissue region for a second duration, wherein one or both of the second energy level and the second duration are based, at least in part, on the determined one or more characteristics of the target tissue region.

17 Claims, 6 Drawing Sheets

(51) Int. Cl.
*A61B 8/00* (2006.01)
*A61B 8/08* (2006.01)
*A61B 17/22* (2006.01)
*A61B 90/00* (2016.01)

(52) U.S. Cl.
CPC ............... *A61B 2017/22008* (2013.01); *A61B 2090/374* (2016.02); *A61B 2090/376* (2016.02); *A61B 2090/378* (2016.02)

(58) Field of Classification Search
USPC .................... 600/407, 437, 439; 601/2, 3, 27
See application file for complete search history.

(56) References Cited

U.S. PATENT DOCUMENTS

| | | |
|---|---|---|
| 3,942,150 A | 3/1976 | Booth et al. |
| 3,974,475 A | 8/1976 | Burckhardt et al. |
| 3,992,693 A | 11/1976 | Martin et al. |
| 4,000,493 A | 12/1976 | Spaulding et al. |
| 4,339,952 A | 7/1982 | Foster |
| 4,454,597 A | 6/1984 | Sullivan |
| 4,478,083 A | 10/1984 | Hassler et al. |
| 4,505,156 A | 3/1985 | Questo |
| 4,526,168 A | 7/1985 | Hassler et al. |
| 4,537,074 A | 8/1985 | Dietz |
| 4,549,533 A | 10/1985 | Cain et al. |
| 4,858,597 A | 8/1989 | Kurtze et al. |
| 4,865,042 A | 9/1989 | Umemura et al. |
| 4,888,746 A | 12/1989 | Wurster et al. |
| 4,889,122 A | 12/1989 | Watmough et al. |
| 4,893,284 A | 1/1990 | Magrane |
| 4,937,767 A | 6/1990 | Reuschel et al. |
| 5,209,221 A | 5/1993 | Riedlinger |
| 5,247,935 A | 9/1993 | Cline et al. |
| 5,271,400 A | 12/1993 | Dumoulin et al. |
| 5,275,165 A | 1/1994 | Ettinger et al. |
| 5,291,890 A | 3/1994 | Cline et al. |
| 5,307,812 A | 5/1994 | Hardy et al. |
| 5,307,816 A | 5/1994 | Hashimoto et al. |
| 5,318,025 A | 6/1994 | Dumoulin et al. |
| 5,323,779 A | 6/1994 | Hardy et al. |
| 5,327,884 A | 7/1994 | Hardy et al. |
| 5,329,930 A | 7/1994 | Thomas, III et al. |
| 5,368,031 A | 11/1994 | Cline et al. |
| 5,368,032 A | 11/1994 | Cline et al. |
| 5,379,642 A | 1/1995 | Reckwerdt et al. |
| 5,391,140 A | 2/1995 | Schaetzle et al. |
| 5,413,550 A | 5/1995 | Castel |
| 5,443,068 A | 8/1995 | Cline et al. |
| 5,474,071 A | 12/1995 | Chapelon et al. |
| 5,485,839 A | 1/1996 | Aida et al. |
| 5,490,840 A | 2/1996 | Uzgiris et al. |
| 5,507,790 A | 4/1996 | Weiss |
| 5,520,188 A | 5/1996 | Hennige et al. |
| 5,526,814 A | 6/1996 | Cline et al. |
| 5,549,638 A | 8/1996 | Burdette |
| 5,553,618 A | 9/1996 | Suzuki et al. |
| 5,573,497 A | 11/1996 | Chapelon |
| 5,582,578 A | 12/1996 | Zhong et al. |
| 5,590,653 A | 1/1997 | Aida et al. |
| 5,590,657 A | 1/1997 | Cain et al. |
| 5,601,526 A | 2/1997 | Chapelon et al. |
| 5,605,154 A | 2/1997 | Ries et al. |
| 5,617,371 A | 4/1997 | Williams |
| 5,617,857 A | 4/1997 | Chader et al. |
| 5,643,179 A | 7/1997 | Fujimoto |
| 5,662,170 A | 9/1997 | Donovan et al. |
| 5,665,054 A | 9/1997 | Dory |
| 5,666,954 A | 9/1997 | Chapelon et al. |
| 5,676,673 A | 10/1997 | Ferre et al. |
| 5,687,729 A | 11/1997 | Schaetzle |
| 5,694,936 A | 12/1997 | Fujimoto et al. |
| 5,711,300 A | 1/1998 | Schneider et al. |
| 5,722,411 A | 3/1998 | Suzuki et al. |
| 5,739,625 A | 4/1998 | Falcus |
| 5,743,863 A | 4/1998 | Chapelon |
| 5,752,515 A | 5/1998 | Jolesz et al. |
| 5,759,162 A | 6/1998 | Oppelt et al. |
| 5,769,790 A | 6/1998 | Watkins et al. |
| 5,810,008 A | 9/1998 | Dekel et al. |
| 5,873,845 A | 2/1999 | Cline et al. |
| 5,897,495 A | 4/1999 | Aida et al. |
| 5,938,600 A | 8/1999 | Van Vaals et al. |
| 5,938,608 A | 8/1999 | Bieger et al. |
| 5,947,900 A | 9/1999 | Derbyshire et al. |
| 5,984,881 A | 11/1999 | Ishibashi et al. |
| 6,004,269 A | 12/1999 | Crowley et al. |
| 6,023,636 A | 2/2000 | Wendt et al. |
| 6,042,556 A | 3/2000 | Beach et al. |
| 6,071,239 A | 6/2000 | Cribbs et al. |
| 6,113,559 A | 9/2000 | Klopotek |
| 6,128,522 A | 10/2000 | Acker et al. |
| 6,128,958 A | 10/2000 | Cain |
| 6,193,659 B1 | 2/2001 | Ramamurthy et al. |
| 6,242,915 B1 | 6/2001 | Hurd |
| 6,263,230 B1 | 7/2001 | Haynor et al. |
| 6,267,734 B1 | 7/2001 | Ishibashi et al. |
| 6,289,233 B1 | 9/2001 | Dumoulin et al. |
| 6,309,355 B1 | 10/2001 | Cain et al. |
| 6,334,846 B1 | 1/2002 | Ishibashi et al. |
| 6,374,132 B1 | 4/2002 | Acker et al. |
| 6,392,330 B1 | 5/2002 | Zloter et al. |
| 6,397,094 B1 | 5/2002 | Ludeke et al. |
| 6,413,216 B1 | 7/2002 | Cain et al. |
| 6,419,648 B1 | 7/2002 | Vitek et al. |
| 6,424,597 B1 | 7/2002 | Bolomey et al. |
| 6,425,867 B1 | 7/2002 | Vaezy et al. |
| 6,428,532 B1 | 8/2002 | Doukas et al. |
| 6,461,314 B1 | 10/2002 | Pant et al. |
| 6,475,150 B2 | 11/2002 | Haddad |
| 6,478,739 B1 | 11/2002 | Hong |
| 6,506,154 B1 | 1/2003 | Ezion et al. |
| 6,506,171 B1 | 1/2003 | Vitek et al. |
| 6,508,774 B1* | 1/2003 | Acker ..................... A61N 7/02 600/439 |
| 6,511,428 B1 | 1/2003 | Azuma et al. |
| 6,522,142 B1 | 2/2003 | Freundlich |
| 6,523,272 B1 | 2/2003 | Morales |
| 6,559,644 B2 | 5/2003 | Froundlich et al. |
| 6,566,878 B1 | 5/2003 | Komura et al. |
| 6,582,381 B1 | 6/2003 | Yehezkeli et al. |
| 6,599,256 B1 | 7/2003 | Acker et al. |
| 6,612,988 B2 | 9/2003 | Maor et al. |
| 6,613,004 B1 | 9/2003 | Vitek et al. |
| 6,613,005 B1 | 9/2003 | Friedman et al. |
| 6,618,608 B1 | 9/2003 | Watkins et al. |
| 6,618,620 B1* | 9/2003 | Freundlich et al. ............ 607/27 |
| 6,626,854 B2 | 9/2003 | Friedman et al. |
| 6,626,855 B1 | 9/2003 | Weng et al. |
| 6,629,929 B1 | 10/2003 | Jago et al. |
| 6,645,162 B2 | 11/2003 | Friedman et al. |
| 6,666,833 B1 | 12/2003 | Friedman et al. |
| 6,676,601 B1 | 1/2004 | Lacoste et al. |
| 6,679,855 B2 | 1/2004 | Horn et al. |
| 6,705,994 B2 | 3/2004 | Vortman et al. |
| 6,719,694 B2 | 4/2004 | Weng et al. |
| 6,733,450 B1 | 5/2004 | Alexandrov et al. |
| 6,735,461 B2 | 5/2004 | Vitek et al. |
| 6,761,691 B2 | 7/2004 | Tsuzuki |
| 6,770,031 B2 | 8/2004 | Hynynen et al. |
| 6,770,039 B2 | 8/2004 | Zhong et al. |
| 6,788,619 B2 | 9/2004 | Calvert |
| 6,790,180 B2 | 9/2004 | Vitek |
| 6,824,516 B2 | 11/2004 | Batten et al. |
| 6,951,540 B2 | 10/2005 | Ebbini et al. |
| 6,961,606 B2 | 11/2005 | DeSilets et al. |
| 7,001,379 B2 | 2/2006 | Behl et al. |
| 7,077,820 B1 | 7/2006 | Kadziauskas et al. |
| 7,094,205 B2 | 8/2006 | Marmarelis |
| 7,128,711 B2 | 10/2006 | Medan et al. |
| 7,175,596 B2 | 2/2007 | Vitek et al. |
| 7,175,599 B2 | 2/2007 | Hynynen et al. |
| 7,264,592 B2 | 9/2007 | Shehada |

(56) References Cited

U.S. PATENT DOCUMENTS

| | | | |
|---|---|---|---|
| 7,264,597 | B2 | 9/2007 | Cathignol |
| 7,267,650 | B2 | 9/2007 | Chow et al. |
| 7,344,509 | B2 | 3/2008 | Hynynen et al. |
| 7,377,900 | B2 | 5/2008 | Vitek et al. |
| 7,505,808 | B2 | 3/2009 | Anderson et al. |
| 7,510,536 | B2 | 3/2009 | Foley et al. |
| 7,511,501 | B2 | 3/2009 | Wexler |
| 7,535,794 | B2 | 5/2009 | Prus et al. |
| 7,553,284 | B2 | 6/2009 | Vaitekunas |
| 7,603,162 | B2 | 10/2009 | Danz et al. |
| 7,611,462 | B2 | 11/2009 | Vortman et al. |
| 7,652,410 | B2 | 1/2010 | Prus |
| 7,686,763 | B2 | 3/2010 | Vaezy et al. |
| 7,699,780 | B2 | 4/2010 | Vitek et al. |
| 2001/0031922 | A1 | 10/2001 | Weng et al. |
| 2002/0035779 | A1 | 3/2002 | Krieg et al. |
| 2002/0082589 | A1 | 6/2002 | Friedman et al. |
| 2003/0004439 | A1 | 1/2003 | Pant et al. |
| 2003/0060820 | A1 | 3/2003 | Maguire et al. |
| 2003/0187371 | A1* | 10/2003 | Vortman et al. .......... 601/3 |
| 2004/0030251 | A1 | 2/2004 | Ebbini et al. |
| 2004/0068186 | A1 | 4/2004 | Ishida et al. |
| 2004/0082857 | A1* | 4/2004 | Schonenberger et al. .... 600/439 |
| 2004/0122323 | A1 | 6/2004 | Vortman et al. |
| 2004/0147919 | A1 | 7/2004 | Behl et al. |
| 2004/0210134 | A1 | 10/2004 | Hynynen et al. |
| 2005/0033201 | A1 | 2/2005 | Takahashi et al. |
| 2005/0038340 | A1* | 2/2005 | Vaezy et al. .......... 600/439 |
| 2005/0096542 | A1 | 5/2005 | Weng et al. |
| 2005/0203444 | A1* | 9/2005 | Schonenberger et al. ........ 601/2 |
| 2005/0240126 | A1* | 10/2005 | Foley et al. ........ 601/2 |
| 2005/0251046 | A1 | 11/2005 | Yamamoto et al. |
| 2006/0052661 | A1 | 3/2006 | Gannot et al. |
| 2006/0052701 | A1 | 3/2006 | Carter et al. |
| 2006/0058678 | A1 | 3/2006 | Vitek et al. |
| 2006/0106300 | A1 | 5/2006 | Seppenwoolde et al. |
| 2006/0173385 | A1 | 8/2006 | Lidgren et al. |
| 2006/0184069 | A1 | 8/2006 | Vaitekunas |
| 2006/0206105 | A1 | 9/2006 | Chopra et al. |
| 2006/0229594 | A1 | 10/2006 | Francischelli et al. |
| 2007/0016039 | A1 | 1/2007 | Vortman et al. |
| 2007/0055140 | A1 | 3/2007 | Kuroda |
| 2007/0055181 | A1 | 3/2007 | Deem et al. |
| 2007/0098232 | A1 | 5/2007 | Matula et al. |
| 2007/0161902 | A1* | 7/2007 | Dan .............. 600/458 |
| 2007/0167781 | A1 | 7/2007 | Vortman et al. |
| 2007/0197918 | A1 | 8/2007 | Vitek et al. |
| 2008/0027342 | A1 | 1/2008 | Rouw et al. |
| 2008/0031090 | A1 | 2/2008 | Prus et al. |
| 2008/0033278 | A1 | 2/2008 | Assif |
| 2008/0082026 | A1 | 4/2008 | Schmidt et al. |
| 2008/0108900 | A1 | 5/2008 | Lee et al. |
| 2008/0183077 | A1 | 7/2008 | Moreau-Gobard et al. |
| 2008/0200845 | A1 | 8/2008 | Sokka et al. |
| 2009/0088623 | A1 | 4/2009 | Vortman et al. |
| 2010/0056962 | A1 | 3/2010 | Vortman et al. |

FOREIGN PATENT DOCUMENTS

| | | | |
|---|---|---|---|
| EP | 0558029 | A3 | 9/1993 |
| EP | 875203 | A2 | 11/1998 |
| EP | 1774920 | A1 | 4/2007 |
| FR | 2806611 | A1 | 9/2001 |
| JP | 11313833 | A | 11/1999 |
| WO | WO-9100059 | A1 | 1/1991 |
| WO | WO-9852465 | A1 | 11/1998 |
| WO | WO-0031614 | A1 | 6/2000 |
| WO | WO0166189 | * | 9/2001 ............... A61N 7/02 |
| WO | WO-0166189 | A1 | 9/2001 |
| WO | WO-0180709 | A2 | 11/2001 |
| WO | WO-02058791 | A1 | 8/2002 |
| WO | WO-03013654 | A1 | 2/2003 |
| WO | WO-03097162 | A2 | 11/2003 |
| WO | WO-03098232 | A2 | 11/2003 |
| WO | WO-0558029 | A2 | 6/2005 |
| WO | WO-2006018837 | A2 | 2/2006 |
| WO | WO-06025001 | A1 | 3/2006 |
| WO | WO-06087649 | A1 | 8/2006 |
| WO | WO-07073551 | A1 | 6/2007 |
| WO | WO-08050278 | A1 | 5/2008 |
| WO | WO-0875203 | A2 | 6/2008 |
| WO | WO-08119054 | A1 | 10/2008 |
| WO | WO-09055587 | A1 | 4/2009 |

OTHER PUBLICATIONS

Cain et al., "Concentric-ring and Sector-vortex Phased-array Applicators for Ultrasound Hperthermia," IEEE Trans. On Microwave Theory & Techniques, vol. MTT-34, No. 5, pp. 542-551 (May 1986).

Chen et al., "MR Acoustic Radiation Force Imaging: Comparison of Encoding Gradients.".

Cline et al., "Focused US system for MR imaging-guide tumor ablation," Radiology, v. 194, No. 3, pp. 731-738 (Mar. 1995).

Cline et al., "MR Temperature mapping of focused ultrasound surgery," Magnetic Resonance in Medicine, vol. 32, No. 6, pp. 628-636 (1994).

Cline et al., "Simultaneous magnetic resonance phase and magnitude temperature maps in muscle," Magnetic Resonance in Medicine, vol. 35, No. 3, pp. 309-315 (Mar. 1996).

Daum et al., "Design and evaluation of a feedback based phased array system for ultrasound surgery," IEEE Trans. Ultrason. Ferroelec. Freq. Control, vol. 45, No. 2, pp. 431-434 (1998).

de Senneville et al., "Real-time adaptive methods for treatment of mobile organs by MRI-controlled high-intensity focussed Ultrasound," Magnetic Resonance in Medicine 57:319-330 (2007).

Fjield et al, "The Combined Concentric-ring and Sector-vortex Phased Array for MRI Guided Ultrasound Surgery," IEEE Trans. On Ultrasonics, Ferroelectrics and Freq. Cont., vol. 44, No. 5, pp. 1157-1167 (Sep. 1997).

Herbert et al., "Energy-based adaptive focusing of waves: application to ultrasonic transcranial therapy," 8th Intl. Symp. On Therapeutic Ultrasound.

Huber et al., "A New Noninvasive Approach in Breast Cancer Therapy Using Magnetic Resonance Imaging-Guided Focussed Ultrasound Surgery," Cancer Research 61, 8441-8447 (Dec. 2001).

International Preliminary Report on Patentability in International Patent Application No. PCT/IB2004/001512, dated Dec. 8, 2005.

International Search Report and Written Opinion in International Patent Application No. PCT/IB2004/001498, dated Aug. 31, 2004.

International Search Report and Written Opinion in International Patent Application No. PCT/IB2005/002273, dated Dec. 20, 2005.

International Search Report and Written Opinion in International Patent Application No. PCT/IB2005/002413, dated Nov. 22, 2005.

International Search Report and Written Opinion in International Patent Application No. PCT/IB2006/001641, dated Sep. 25, 2006.

International Search Report and Written Opinion in International Patent Application No. PCT/IB2006/003300, dated Feb. 14, 2008.

International Search Report and Written Opinion in International Patent Application No. PCT/IB2007/001079, dated Dec. 10, 2007.

International Search Report and Written Opinion in International Patent Application No. PCT/IB2007/002134, dated Dec. 13, 2007.

International Search Report and Written Opinion in International Patent Application No. PCT/IB2007/002140, dated Dec. 29, 2008.

International Search Report and Written Opinion in International Patent Application No. PCT/IB2008/003069, dated Apr. 27, 2009.

Jolesz et al., "Integration of interventional MRI with computer-assisted surgery," J. Magnetic Resonance Imaging. 12:69-77 (2001).

Kohler et al., "Volumetric HIFU Ablation guided by multiplane MRI thermometry," 8th Intl. Symp. On Therapeutic Ultrasound, edited by E.S. Ebbini, U. of Minn. (Sep. 2009).

Kowalski et al., "Optimization of electromagnetic phased-arrays for hyperthermia via magnetic resonance temperature estimation," IEEE Trans. On Biomed. Eng., vol. 49, No. 11, pp. 1229-1241 (Nov. 2002).

Maxwell et al., "Noninvasive thrombolysis using pulsed ultrasound cavitation therapy—Histotripsy," Abstract, U.S. Natl. Lib. Of Med., NIH, Ultrasound Med. Biol. (Oct. 23, 2009).

(56) References Cited

OTHER PUBLICATIONS

McDannold et al., "MRI evaluation of thermal ablation of tumors and focused ultrasounds," JMRI vol. 8, No. 1, pp. 91-100 (1998).
McDannold et al., "Magnetic resonance acoustic radiation force imaging," Med. Phys. vol. 35, No. 8, pp. 3748-3758 (Aug. 2008).
Medel et al., "Sonothrombolysis: An emerging modality for the management of stroke," Neurosurgery, vol. 65, No. 5, pp. 979-993.
Mougenot et al., "MR monitoring of the near-field HIFU heating," 8th Intl. Symp. On Therapeutic Ultrasound, edited by E.S. Ebbini, U. Of Minn. (Sep. 2009).
Partial International Search Report and Written Opinion in International Patent Application No. PCT/IB2007/001079, dated Sep. 25, 2007.
Vimeux et al., "Real-time control of focused ultrasound heating based on rapid MR thermometry," Investig. Radiology, vol. 43, No. 3, pp. 190-193.
Vykhodtseva et al., "MRI detection of the thermal effects of focused ultrasound on the brain," Ultrasound in Med. & Biol., vol. 26, No. 5, pp. 871-880 (2000).
Written Opinion in International Patent Application No. PCT/IL01/00340, dated Feb. 24, 2003.
Written Opinion in International Patent Application No. PCT/IL02/00477, dated Feb. 25, 2003.
Written Opinion in International Patent Application No. PCT/IB03/05551, dated Sep. 10, 2004.
"How is Ablathemi treatment performed?" http://www.edap-hifu.com/eng/physicians/hifu/3c_treatment_treat-description.htm, accessed Jan. 3, 2003.
"What is HIFU? HIFU: High Intensity Focused Ultrasound," http://www.edap-hifu.com/eng/physicians/hifu2a_hifu_overview.htm, accessed Jan. 3, 2003.
"What are the physical principles?" http://www.edap-hifu.com/eng/physicians/hifu/2c_hifu_physical.htm, accessed Jan. 3, 2003.
"How does HIFU create a lesion?" http://www.edap-hifu.com/eng/physicians/hifu/2d_hifu_lesion.htm, accessed Jan. 3, 2003.
"Prostate Cancer Phase I Clinical Trials Using High Intensity Focused Ultrasound (HIFU)," Focus Surgery, http://www.focus-surgery.com/PCT%20Treatment%20with%20HIFU.htm, accessed Jan. 3, 2003.
"Abstract" Focus Surgery, http://www.focus-surgery.com/Sanghvi.htm, accessed Jan. 3, 2003.
Exablate 2000 Specification, InSightec, Ltd. (2 pages).
FDA Approves Exablate 2000 as Non-invasive surgery for Fibroids, Oct. 22, 2004.
International Search Report and Written Opinion in International Patent Application No. PCT/IB2010/000189, dated Jun. 1, 2010.
International Application Serial No. PCT/IB2003/005551, International Search Report dated Mar. 9, 2004, 3 pages.
International Application Serial No. PCT/IB2010/000971, International Search Report and Written Opinion dated Jul. 29, 2010, 9 pages.
Office Action dated Apr. 29, 2010 for Chinese Patent Application No. 200680029730.8, English translation of "Notification of Reason for Rejection", 7 pages.

\* cited by examiner

Cause the delivery of a first level of ultrasound energy to the target tissue region for a first duration resulting in the generation of micro-bubbles in the target tissue region Detect activity of the micro-bubbles, if present, based on an acoustic signal therefrom Cause a modality to transmit a signal to the target tissue region and detect a response, if present, therefrom Determine (i) whether the activity of the micro-bubbles is detected and the response from the target tissue is not detected and (ii) whether the activity of the micro-bubbles is not detected and the ultrasound energy to be delivered varies non-linearly with time Suspend the delivery of the ultrasound energy to the target tissue region if (i) or (ii) is determined to occur

FIG. 5

CONTROLLED, NON-LINEAR FOCUSED ULTRASOUND TREATMENT

RELATED APPLICATION DATA

This application is a U.S. National Stage filing under 35 U.S.C. § 371 of International Application No. PCT/IB2006/001641, filed Jun. 19, 2006, which claims priority to U.S. patent application Ser. No. 11/158,657, filed Jun. 21, 2005. This application is a continuation-in-part of U.S. patent application Ser. No. 11/158,657. Priority to the aforementioned application is hereby expressly claimed in accordance with 35 U.S.C. §§ 119, 120, 365 and 371 and any other applicable statues.

FIELD OF INVENTION

This invention relates generally to systems for delivering focused ultrasound energy to targeted tissue regions in a patient's body.

BACKGROUND

High intensity focused ultrasonic energy (i.e., having a frequency greater than about 20 kilohertz), may be used therapeutically to treat internal tissue regions within a patient. For example, ultrasonic waves may be used to induce coagulation and/or necrosis in a target tissue region, such as a tumor. In this process, the ultrasonic energy is "absorbed" by the tissue, causing the generation of heat. The absorbed energy heats the targeted tissue cells to temperatures that exceed protein denaturation thresholds, usually above 60° C., resulting in coagulation and/or necrosis of the tissue.

During a focused ultrasound procedure, small gas bubbles, or "micro-bubbles," may be generated in the liquid contained in the tissue, due to the stress resulting from negative pressure produced by the propagating ultrasonic waves and/or from when the heated liquid ruptures and is filled with gas/vapor. On the one hand, the micro-bubbles have a positive treatment effect by generating higher harmonic frequencies of the original wave energy, thereby increasing the absorption of energy in the tissue, and by multiple reflection that extends the acoustic pass in the target region. On the other hand, the reaction of tissue containing a higher relative percentage of micro-bubbles to the continued application of the ultrasound energy is non-linear and difficult to predict. For example, the micro-bubbles may collapse due to the applied stress from an acoustic field. This mechanism, called "cavitation," may cause extensive tissue damage beyond that targeted, and may be difficult to control.

SUMMARY OF THE INVENTION

In accordance with one embodiment of the invention, a system for treating tissue within a body includes means for delivering a first level of ultrasound energy to a target tissue region for a first duration resulting in the generation of micro-bubbles in the target tissue region, means for determining one or more characteristics of the target tissue region in the presence of the micro-bubbles, and means for delivering a second level of ultrasound energy to the target tissue region for a second duration, wherein one or both of the second energy level and second duration are based, at least in part, on the determined one or more characteristics of the target tissue region.

BRIEF DESCRIPTION OF THE DRAWINGS

Various embodiments of the invention are described hereinafter with reference to the accompanying figures, in which.

DETAILED DESCRIPTION OF THE ILLUSTRATED EMBODIMENTS

Figure 1A:
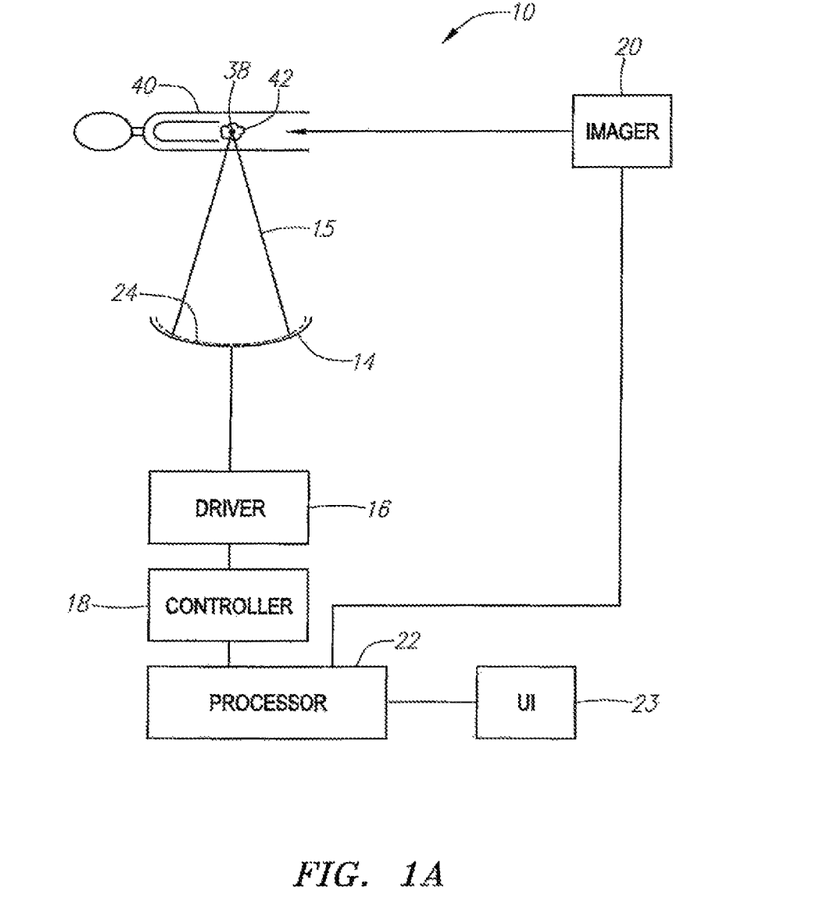
FIG. 1A illustrates a focused ultrasound system, including an ultrasound transducer for focusing ultrasonic energy at a target tissue region within a patient.

FIG. 1A illustrates a focused ultrasound system 10 in accordance with embodiments of the invention. The system 10 includes an ultrasound transducer 14, drive circuitry (driver) 16 coupled to the transducer 14, a controller 18 coupled to the driver 16, an imaging device 20, and a processor 22 coupled to the respective imaging device 20 and controller 18. The transducer 14 is used to delivery high intensity, focused acoustic energy (represented by beam 15) to a focal zone 38 located in a target tissue region 42, typically a tumor, within a patient 40. The system 10 also includes a user interface (UI) 23, such as one or more of a screen, keyboard, a mouse, a button, a touch pad, and the like, for allowing a user to input data, such as treatment parameters, to the processor 22. The user interface 23 is shown as a separate component from the processor 22. Alternatively, the user interface 23 can be integrated with the processor 22. One or more memories is also associated with the processor, as is well-known in the art.

The transducer 14 may comprise a multiplicity of individual piezoelectric elements 24 that collectively form a two-dimensional phased transducer array. In alternate embodiments, the transducer 14 may comprise a single transducer element. In some embodiments, the transducer 14 may have a concave or bowl shape, such as a "spherical cap" shape having a substantially constant radius of curvature such that the transducer 14 has an inside surface defining a portion of a sphere. Alternatively, the transducer 14 may have a substantially flat configuration (not shown), and/or may include an outer perimeter that is generally, but not necessarily, circular.

The transducer 14 may be divided into any desired number of elements (not shown), which may be disposed about a central axis, preferably but not necessarily, in a substantially uniform or symmetrical configuration. In the illustrated embodiments, each of the transducer elements 24 may be a one-piece piezo-ceramic part, or alternatively, be composed of a mosaic arrangement of a plurality of small piezoceramic elements that are electrically coupled to a same drive signal. The transducer elements 24 are preferably individually controlled (e.g., phase, amplitude, frequency), as is described in U.S. Pat. No. 6,506,154. The actual configuration of the transducer 14, however, is not important for purposes of understanding the invention, and any of a variety of ultrasound transducers may be employed, such as flat circular arrays, linear arrays, and the like.

The transducer 14 may be mounted within a casing or chamber (not shown) filled with degassed water or acoustically transmitting fluid. The chamber may be located within a table (not shown) upon which a patient 40 may be positioned, or within a fluid-filled bag mounted on a movable arm that may be placed against a patient's body. The contact surface of the chamber, generally includes a flexible membrane (not shown) that is substantially transparent to ultrasound. For examples, the flexible member may be constructed from mylar, polyvinyl chloride (PVC), or other suitable plastic material. A fluid-filled bay (not shown) may be provided on the membrane that may conform easily to the contours of the patient 40 positioned on the table, thereby acoustically coupling the patient 40 to the transducer 14 within the chamber. In addition or alternatively, acoustic gel, water, or other fluid may be provided between the patient 40 and the membrane to facilitate further acoustic coupling between the transducer 14 and the patient 40.

In the illustrated embodiments, the transducer elements 24 are coupled to the driver 16 and/or controller 18 for generating and/or controlling the acoustic energy emitted by the transducer elements 24. In particular, the driver 16 generates one or more electronic drive signals under the control of the controller 18. The transducer elements 24 convert the electronic drive signals into acoustic energy 15, which may be focused using conventional methods. The controller 18 and/or driver 16 may be separate or integral components. The operations performed by the controller 18 and/or driver 16 may be performed by one or more controllers, processors, and/or other electronic components, including software and/or hardware components. The terms controller and control circuitry may be used herein interchangeably, and the terms driver and drive circuitry may be used herein interchangeably.

The driver 16, which may be an electrical oscillator, generates drive signals in the ultrasound frequency spectrum, e.g., as low as fifty kilohertz (20 KHz), or as high as ten megahertz (10 MHz), and more preferably, between 0.1 to 10 MHz. Preferably, the driver 16 provides drive signals to the transducer elements 24 at radio frequencies (RF), for example, between about a hundred Kilohertz to ten Megahertz (0.1-10 MHz), and more preferably between 200 Kilohertz and three Megahertz (0.20 and 3.0 MHz). However, in other embodiments, the driver 16 can also be configured to operate in other ranges of frequencies. When the drive signals are provided to the transducer elements 24, the transducer elements 24 emit acoustic energy 15 from their respective exposed surfaces.

The controller 18 may control a phase component of the drive signals to respective elements 24 of the transducer 14, e.g., to control a shape of a focal zone 38 generated by the transducer 14 and/or to move the focal zone 38 to a desired location. For example, the controller 18 may control the phase shift of the drive signals based upon a radial position of respective transducer elements 24 of the transducer 14, e.g., to adjust a focal distance, or to adjust phases to control the focus lateral position. In addition or alternatively, the controller 18 may control the positioning system to move the transducer 14, and consequently, the location of the focal zone 38 of the transducer 14, to a desired location (e.g., within the target tissue region 42).

In some embodiments, the controller 18 may also control a frequency and/or amplitude (and/or other aspects) of the drive signals, and therefore, the intensity or power of the acoustic wave energy transmitted by the transducer elements 24. For example, the controller 18 may cause the drive circuitry 16 to output respective drive signals to the transducer 14 above a threshold such that the acoustic energy emitted by the transducer 14 will generate micro-bubbles within tissue in the focal zone 38. Subsequently, the controller 18 may lower the intensity below the threshold and to a level at which the generation of micro-bubbles is minimized in the tissue within the focal zone 38, yet still sufficient to therapeutically treat (e.g. necrose) the tissue, as explained below.

The controller 18 also preferably controls the respective transducer elements 24 to protect a tissue region (e.g., healthy tissue) that is located adjacent to the target tissue 42, at the far field relative to the target tissue 42, or at the near field relative to the target tissue 42, while still effectively treating the target tissue. Particularly, the controller 18 is configured to control an amplitude, a phase, a frequency, or a combination thereof, of respective transducer elements 14, such that an energy intensity at the target tissue 42 is above a prescribed threshold (treatment threshold) level sufficient to treat the target tissue 42, while an energy intensity at tissue (sensitive tissue) desired to be protected is below a prescribed threshold (safety threshold) level for protection of the sensitive tissue. For examples, the controller 18 can generate a drive signal to reduce an energy delivered to the sensitive tissue by one of the transducer elements 24, or not activate one of the transducer elements 24, thereby creating a zone of relatively lower energy at the sensitive tissue. As used herein, the term, "sensitive tissue" refers to tissue that is desired to be protected, and should not be limited to tissue have a certain sensitivity.

In the illustrated embodiments, the imaging device 20 is configured for obtaining image data of at least a portion of the target region 42 before or while treating the patient 40. For example, the imaging device 20 may be a magnetic resonance imaging (MRI) device, such as that disclosed in U.S. Pat. Nos. 5,247,935, 5,291,890, 5,368,031, 5,368,032, 5,443,068, 5,307,812, 5,323,779, and 5,327,884. In other embodiments, the imaging device 20 can be another type of device capable of performing an imaging of tissue, such as, a x-ray device, a fluoroscope, an ultrasound imaging device, or a computed tomography machine. Although the imaging device 20 is shown separated from the transducer device 14, in alternative embodiments, the imaging device 20 can be a component of, or integrated with, the transducer device 14. For example, the imaging device 20 can be secured to a center of the transducer device 14 in some embodiments. Also, the term "image" as used herein is intended to include image data that may be stored in a circuitry or a computer-readable medium, and is not limited to image data that is displayed to be visually perceived.

During use of the system 10, image data obtained from the imaging device 20 are transmitted to processor 22 for processing. In some embodiments, the processor 22 can be a computer, or a component of a computer. As used herein, the term, "computer" is not limited to desktop computers and laptops, and includes any device capable of performing the functions described herein. For example, the processor 22 can be a general purpose processor, or an application specific processor (e.g., an ASIC processor, DSP, etc.). In further embodiments, the processor 22 can be a software (an example of a computer product), or a combination of a software and a hardware. In FIG. 1A, the processor 22 is shown as a separate component from the driver 16 and the controller 18. Alternatively, the processor 22 can be a component of the driver 16, and/or a component of the controller 18.

After receiving image data from the imager 20, the processor 22 may use the image data (along with other factors) to construct a treatment plan, in which case, the processor 22 functions as a planner. When functioning as a planner, the processor 22 may automatically construct a treatment plan, which consists of a series of treatment sites represented by thermal dose properties. The treatment plan may also be constructed based, at least in part, on user inputs. The purpose of the treatment plan is to ensure complete ablation of target mass 42 by planning a series of sonications that will apply a series of thermal doses at various points within target mass 42, resulting in a composite thermal dose sufficient to ablate the entire mass 42.

For example, the plan will include the location, frequency, duration, and power of the sonication and the position and mode of the focal spot for each treatment site in series of treatment sites. The mode of the focal spot refers to the fact that the focal spot can be of varying dimensions. Typically, there will be a range of focal modes from small to large with several intermediate modes in between. The actual size of the focal spot will vary, however, as a function of the focal distance (I), the frequency, and focal spot dispersion mode that could be generated by spatial dithering of the focus or by shaping of the focus acoustically. While planning, the processor 22 may take the tissue data in the pass zone, types of tissues, frequency, mode and focal spot size variation into account when planning the position of the focal spot for a treatment site, the required power level and energy level. The treatment plan is then passed to the controller 18 in the relevant format to allow the controller 18 to perform its tasks.

In order to construct the treatment plan, the processor 22 receives input(s) from the user interface 23 and the imager 20. For example, in one implementation, a user specifies the target volume, the clinical application protocol, i.e., breast, pelvis, eye, prostate, etc., via the user interface 23. Selection of the clinical application protocol may control at least some of the default thermal dose prediction properties such as thermal dose threshold, thermal dose prediction algorithm, maximum allowed energy density, thermal dose for different treatment site, cooling time between thermal doses, etc.

In other implementations, some or all of these properties are input through the user interface 23 as user specified thermal dose prediction properties. Other properties that may be input as user specified thermal dose prediction properties are the sonication grid density (how much the sonications should overlap) and the physical parameters of transducer 14. The latter two properties may also be defined as default parameters in certain implementations. Additionally, a user may edit any of the default parameters via the user interface 23. In one implementation, user interface 23 comprises a Graphical User Interface (GUI): A user employs a mouse or touch screen to navigate through menus or choices as displayed on a display device in order to make the appropriate selections and supply the required information.

Figure 1B:
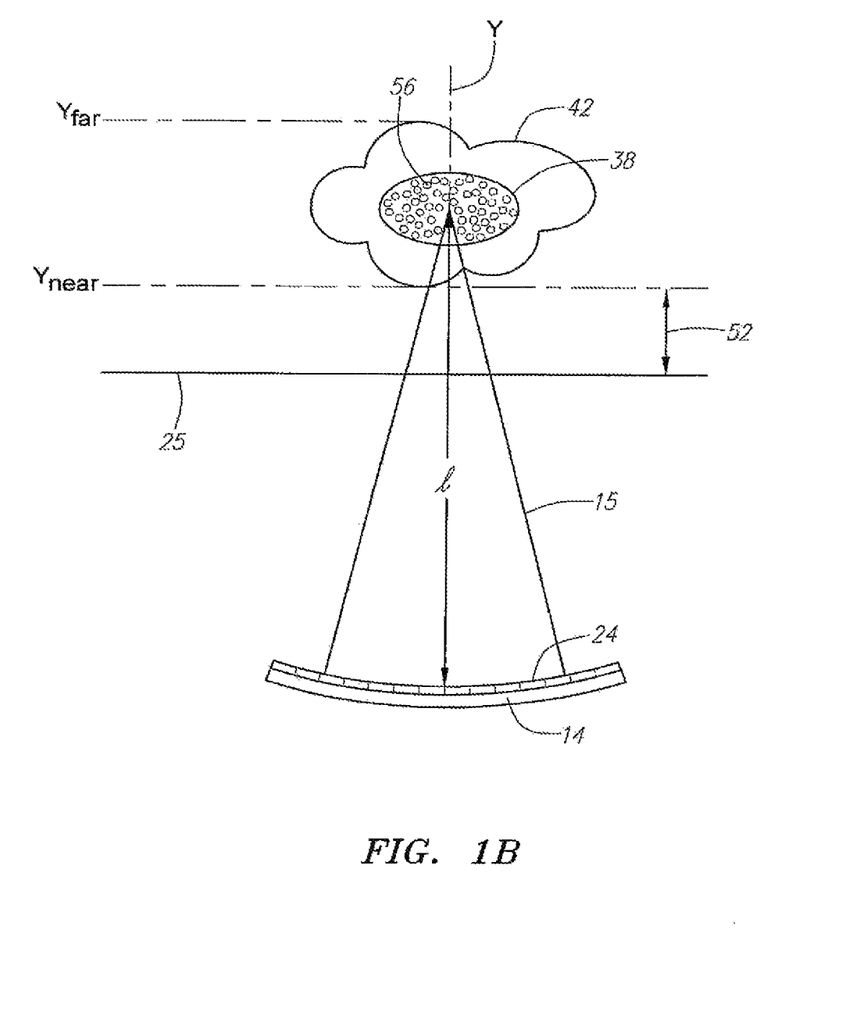
FIG. 1B is a cross-sectional detail of the ultrasonic transducer and target tissue region of FIG. 1A, illustrating micro-bubbles generated in tissue located in a focal zone of the transducer.

To further aid the processor 22 in constructing the treatment plan, the imager 20 supplies image data of the target mass 42 that can be used to determine volume, position, and distance from a skin surface 25 (FIG. 1B). In one implementation, the imager 20 is a MRI device and the images provided are three-dimensional images of the target mass 42. Once the processor 22 receives the input from the user interface 23 and the image data from the imager 20, the processor 22 automatically constructs the treatment plan.

Figure 2:
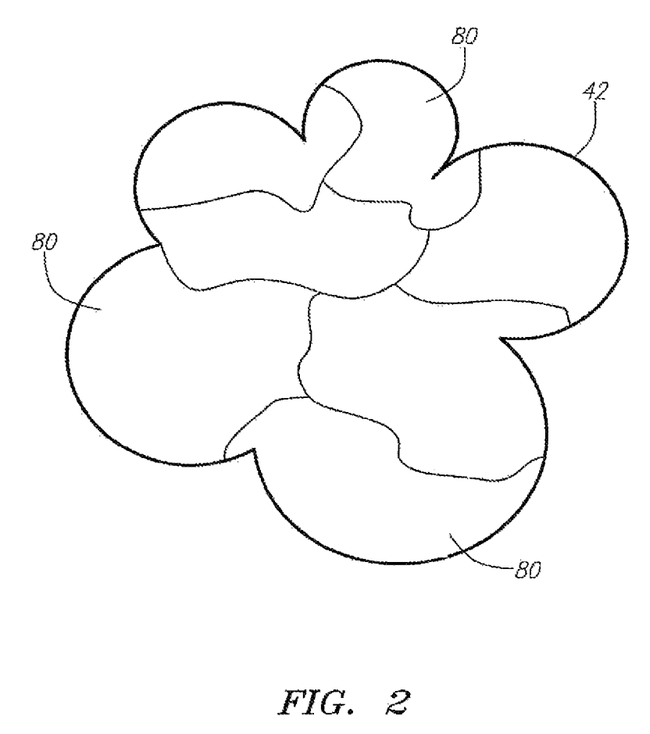
FIG. 2 is a cross-sectional view of a target tissue mass, illustrating a series of planned sonication areas.

As illustrated in FIG. 2, the goal of the treatment plan is to completely cover a target tissue mass 42, and a predefined margin around it if so desired, by delivering a series of sonications to treat a plurality of portions 80 of the target tissue mass 42, so that the entire target mass 42 is fully ablated. In one implementation, once the treatment plan is constructed, a user may, if required, edit the plan by using the user interface 23. In one implementation, the processor 22 will also produce a predicted thermal dose distribution. This distribution is similar to the distribution illustrated in FIG. 2, wherein the predicted thermal doses are mapped onto images of target mass 42 provided by the imager 20. In one implementation, the distribution is a three-dimensional distribution. In some embodiments, an algorithm is included in the processor 22 that limits the peak temperature of the focal zone 38. The algorithm is referred to as the dose predictor.

Figure 3:
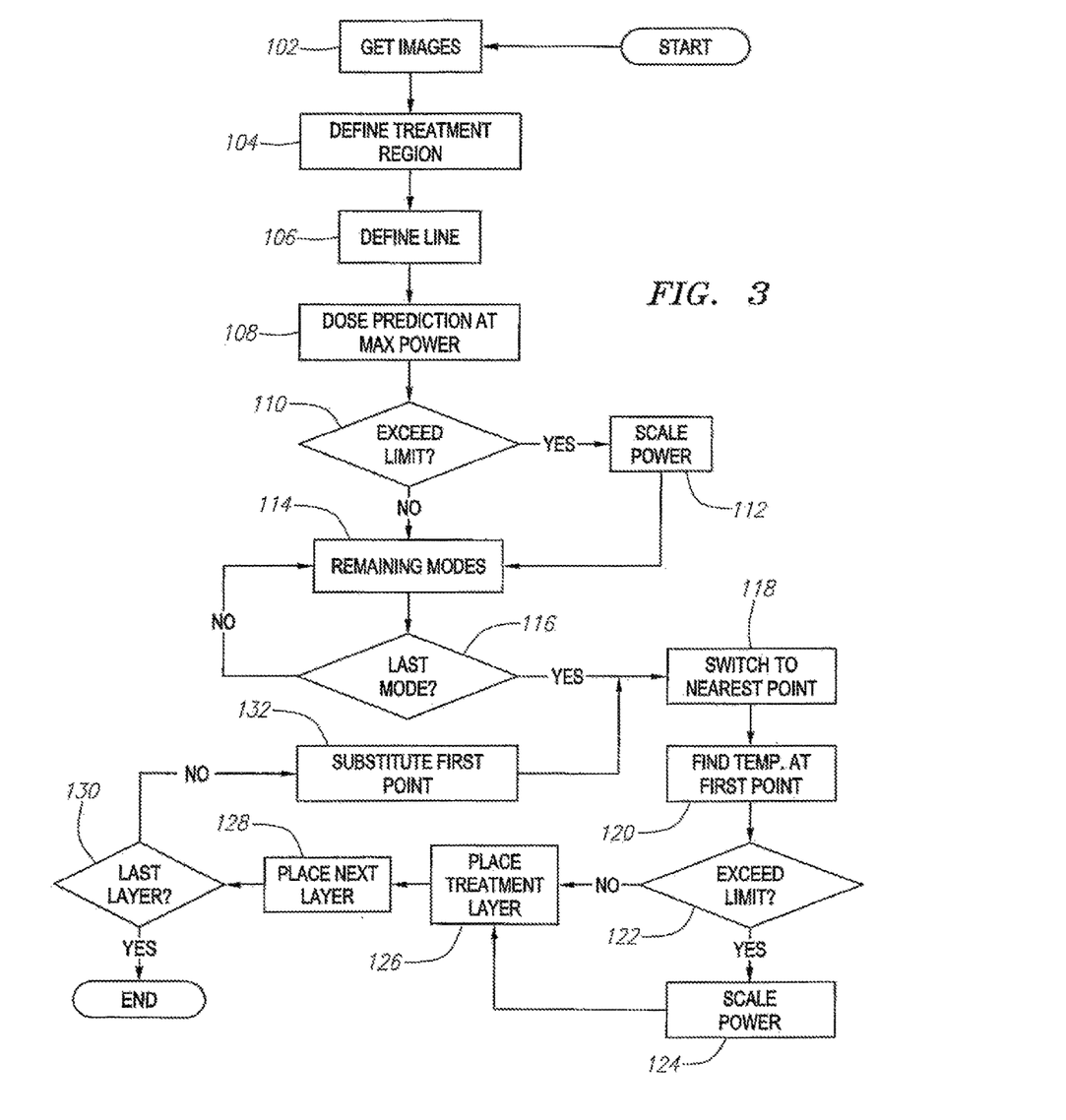
FIG. 3 is a flow chart depicting construction of a treatment plan to be carried out using embodiments of the invention.

FIG. 3 illustrates one process flow diagram for constructing a three-dimensional treatment plan, using three-dimensional images of the target mass 42 and a three-dimensional predicted thermal dose distribution. The ability of focusing at different focal lengths (I) leads to variable focal spots and variable lesion sizes in the target mass 42 as a function of (y), the transducer axis (FIG. 1B). Therefore, as a result of the process illustrated in FIG. 3, the processor 22 finds a minimum number of overlapping cross-sectional treatment layers required to ablate a portion of the target mass 42 extending from (y) near to (y) far. The processor 22 may also predict the lesion size in the cross-sectional layer and will provide the maximal allowed energy in each layer, taking into account the maximum allowed temperature rise. The energy or power will be normalized among different layers, such that the maximal temperature at the focus remains approximately constant throughout the treatment zone.

Constructing the three-dimensional treatment plan begins in step 102 with obtaining diagnostic quality images of the target mass 42. For example, the diagnostic quality images may be the preliminary images supplied by an imager such as the imager 20. In step 104, the processor 22 uses the diagnostic images to define the treatment region, or the user may define it through the user interface 23. Then, in step 106, a line y=[ynear:yfar] is defined such that (y) cuts through target zone perpendicular to the transducer 14 along the transducer axis from the nearest point within the target mass 42 (ynear) to the furthest point (yfar). Line (y) will be the axis along which the treatment layers will be defined.

Once (y) is defined, the processor 22 will perform a dose prediction in step 108 using the maximal power required for small and large spot sizes at (yfar). In step 110, the processor 22 determines if the resulting maximal temperature exceeds the allowed limit. It should be noted that properties such as the maximal power and the maximal temperature limit may be supplied as default thermal dose prediction properties or may be supplied as user supplied thermal dose prediction properties. If the resulting maximal temperature does exceed the allowable limit, the power is scaled down linearly in step 112 until the temperature elevation is within the allowable limit, or until some other predefined threshold is crossed.

The small and large focal modes may correspond to modes 0 and 4, respectively, with additional modes 1, 2 and 3 falling between modes 0 and 4. Therefore, in step 114, the processor 22 predicts the maximal power for the intermediate modes 1, 2 and 3, from the scaled max powers at modes 0 and 4. Thus, in step 116, if there are further modes, the processor 22 reverts to step 108 and predicts the maximal power for these modes. If it is the last mode for (yfar) then the processor 22 uses the same scaled max power, as in step 118, to find the corresponding maximal powers for each focal mode at (ynear). Then in step 120, the processor 22 finds the maximal temperature elevation and lesion size for the appropriate mode and the required maximal power at a point (yl), such that ynear<yl<yfar. Preferably, (yl) is close to (ynear). For example, in one implementation, yl=ynear+ 25 mm. If the temperature elevation at (yl) exceeds the allowable limit as determined in step 122, then in step 124 the power is scaled down until the temperature elevation is within the limit, and then the processor 22 determines the resulting lesion size at (yl).

Using an overlap criterion with respect to the (ynear) boundary, which may be provided via a sonication grid density, the first treatment is placed (step 126). Of course, the treatment will actually be a three-dimensional volume. Then, in step 128, using an inter-layer overlap criterion, an auxiliary treatment slice is placed on top of the previous treatment layer using the same height for the second slice as for the first slice. In step 130, the processor 22 determines if more layers are needed to reach (yfar). If more layers are needed, then the process reverts to step 118, and (yl) replaces (ynear) (step 132) in the algorithm.

Once the last treatment layer is reached, the processor 22 will determine if the layer extends beyond the target limit (yfar). If the layer does extend too far, then the overlap criterion should be used with the outer limit (yfar) as a boundary instead of the previous layer. Using (yfar) in the overlap criterion may cause overdose but will not damage healthy tissue outside target mass 42. In one implementation, the thermal dose properties are automatically optimized using physiological parameters as the optimization criterion. For example, mechanical tissue parameters like compressibility, stiffness, and scatter, may be used.

In still further embodiments, the processor 22 does not construct the treatment plan, but instead, the processor 22 is configured to receive a pre-determined treatment plan via an input (e.g., a disk drive, a cable port, a USB port, a phone port, a memory slot, etc.).

After a treatment plan has been obtained, the system 10 can then be used to treat the patient 40. During use, the patient 40 may be positioned on the table with water, acoustically conductive gel, and the like applied between the patient 40 and the bag or membrane, thereby acoustically coupling the patient 40 to the transducer 14. The transducer 14 may be focused towards a target tissue region 38 within a tissue 42, which may, for example, be a cancerous or benign tumor. The transducer 14 may be activated by supplying a set of drive signals at one or more frequencies to the transducer 14 to focus acoustic energy at the target tissue 42, represented by energy beam 15. As the acoustic energy 15 passes through the patient's body, a fraction of the acoustic energy 15 is converted to heat, which may raise the temperature of the target tissue 42. The acoustic energy 15 may be focused on the target tissue 42 to raise the temperature of the target tissue 42 sufficiently to coagulate and/or necrose the tissue 42, while minimizing damage to surrounding healthy tissue.

In order to optimize a therapeutic procedure, the system 10 may be operated to achieve a maximal coagulation rate (coagulated tissue volume/time/energy) in the target tissue 42, while minimizing heating in the surrounding tissue, particularly within the near field region 52, as well as in the far field. The coagulation rate may be optimized by achieving preferential absorption of the ultrasonic waves, where the absorption by the tissue within the focal zone 38 is higher than the tissue outside the focal zone 38. The presence of micro-bubbles 56 in tissue within the focal zone 38 (shown in FIG. 1B) helps to achieve this goal, because the presence of micro-bubbles 56 in the tissue results in a higher energy absorption coefficient than in the surrounding tissue without micro-bubbles.

Figure 4:
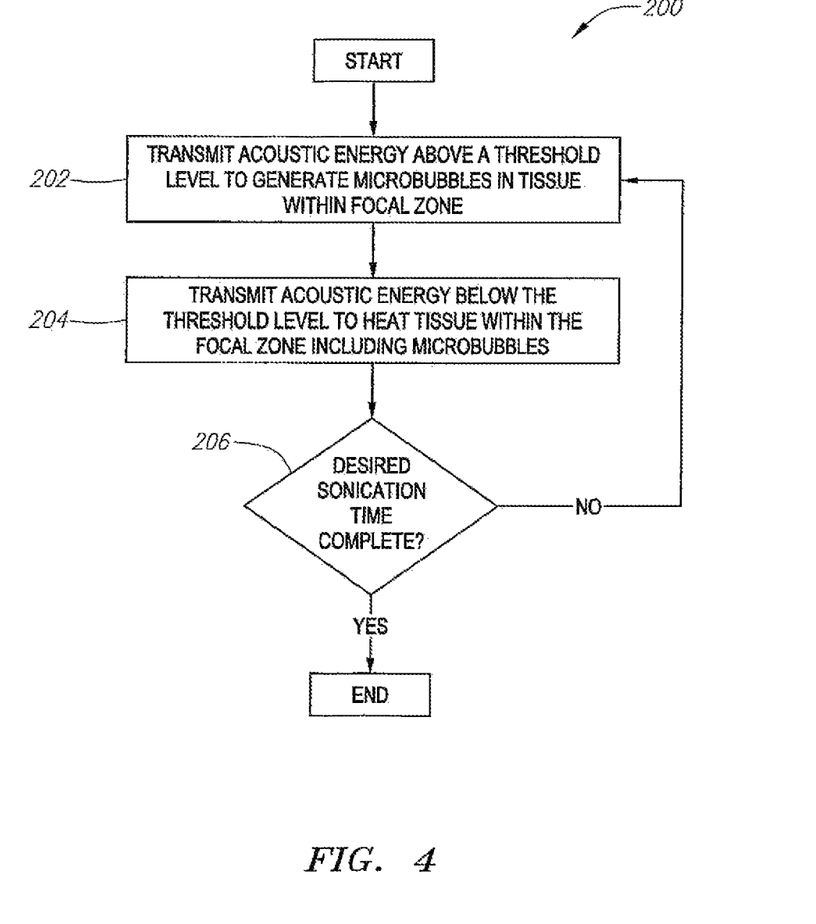
FIG. 4 is a flow chart of a micro-bubble enhanced ablation process carried out using embodiments of the invention.

FIG. 4 illustrates the method 200 for heating tissue within a target region, e.g., to induce tissue coagulation and/or necrosis during a sonication that includes a series of acoustic energy transmissions at different intensities. Initially, a target tissue 42, e.g., a benign or malignant tumor within an organ, such as a liver, kidney, uterus, breast, brain, and the like, may be selected for treatment. At step 202, ultrasonic waves above a certain threshold intensity are directed towards the target tissue structure 42 to generate micro-bubbles 56 within the focal zone 38. Although this threshold intensity may differ with each patient and/or tissue structure, appropriate threshold intensities may be readily determined, e.g., through the use of a monitoring mechanism sensitive to the generation of micro-bubbles.

Transmission of acoustic energy at the intensity above the threshold level required to generate micro-bubbles may be relatively brief, e.g., having a duration of about three seconds or less, and preferably having a duration of not more than about 0.1-0.5 second, yet sufficiently long to generate micro-bubbles within the focal zone 38 without substantially generating micro-bubbles in tissue outside the focal zone 38, e.g., in the near field 52 (shown in FIG. 1B). The micro-bubbles generated in the focal zone 38 oscillate at the frequency of the delivered acoustic waves, and assist in extending the acoustic pass in the focus area by multiple reflections and/or acting as non linear multipliers that receive energy at a lower frequency and transmit it back at a higher frequency and/or generating some limited local cavitation, hence enhancing absorption of the energy at the focal volume. This allows tissue within the focal zone 38 to be heated faster and more efficiently, than would otherwise occur without the presence of the micro-bubbles.

At step 204, the intensity of the beam 15 is lowered below the threshold level and, maintained at a lower intensity while the beam 15 remains focused substantially at the focal zone 38 so as to heat the tissue within the focal zone 38 without collapsing the micro-bubbles 56 within the focal zone 38. By way of one example, this lower intensity level may be reduced below the intensity used to generate the micro-bubbles 56 by a factor of about two to three. Transmission at this lower intensity may have a substantially longer duration as compared to the transmission at the higher intensity used to generate the micro-bubbles 56.

By way of another example, the "lower intensity" acoustic energy may be transmitted for at least about two or three seconds (2-3 s.), and preferably about eight to ten seconds (8-10 s.). By way of further example, micro-bubbles 56 generated within tissue may be present for as little as eight to ten seconds (8-10 s.), e.g., due to natural perfusion of the tissue. Thus, the acoustic energy may be maintained for as long as sufficient supply of micro-bubbles are present. Because of the micro-bubbles 56, acoustic energy absorption by the tissue within the focal zone 38 may be substantially enhanced, as explained above.

At step 206, the controller 18 may determine whether the sonication has been sufficiently long to heat the tissue within the focal zone 38 to a desired level, e.g., to coagulate or otherwise necrose the tissue within the focal zone 38. If not, additional micro-bubbles may be generated in the target tissue region, e.g., by repeating step 202, and then the intensity may be reduced to heat the tissue while avoiding causing collapse of micro-bubbles, e.g., by repeating step 164 or by using temporally spaced short high power transmissions. Steps 202 and 204 may be repeated periodically, e.g., one or more times, during the sonication until sufficient time has passed to substantially ablate or otherwise treat the tissue within the focal zone 38.

Thus, a single sonication, which may last between one and twenty seconds (1-20 s.), and preferably, about ten seconds (10 s.) or more, may include multiple transmissions above and below the threshold necessary to generate micro-bubbles. For example, after perfusion has at least partially dispersed the micro-bubbles from the tissue within the focal zone 38, transmission at an intensity above the threshold level may be repeated in order to maintain a level of micro-bubble density sufficient to create preferential absorption of the tissue within the focal zone. Transmission of acoustic energy at an intensity below the threshold level may then be repeated to cause heating of the tissue within the focal zone without causing bubble collapse. The intensity levels of the acoustic energy may be set to switch between an increment above and an increment below the threshold intensity, or to switch between on and off periods. Alternatively, the intensities may be varied during the course of the sonication. This alternating sequence of acoustic transmissions may be localized and timed in such a way as to create and maintain a micro-bubble "cloud" in the target tissue 42 to optimize the coagulation process.

This alternating sequence during a single sonication may provide several advantages as compared to conventional focused ultrasound ("FUS") ablation without micro-bubbles. For example, if an intensity level is utilized in the heating, while minimizing the bubble collapse step (step 204) that is comparable to conventional FUS ablation, a substantially larger focal zone 38 may created. For example, due to the enhanced energy absorption, the resulting focal zone 38 may be about two to three times larger than conventional FUS ablation utilizing the same energy, thereby necrosing or otherwise heating a larger volume of tissue within the target tissue 42. This increased ablation volume may result in requiring fewer sonications to ablate an entire target tissue 42.

Alternatively, a lower intensity level may be used as compared to conventional FUS, thereby generating a comparably sized focal zone while using substantially less energy. This may reduce energy consumption by the system 10 and/or may result in substantially less energy being absorbed by surrounding tissue, particularly in the near field 52. With less energy absorbed, cooling times between sonications may be substantially reduced. For example, where conventional FUS may require ninety seconds or more of cooling time between sonications, systems and methods in accordance with embodiments described herein may allow cooling times of about forty seconds or less. Thus, in either case, an overall treatment time to ablate or otherwise treat a target tissue structure may be substantially reduced as compared to conventional FUS without micro-bubbles.

Upon completing a sonication, the transducer 14 is deactivated, e.g., for sufficient time to allow heat absorbed by the patient's tissue to dissipate. The transducer 14 may then be focused on another portion of the target tissue region 42, e.g., adjacent the previously treated tissue, and the process 200 is repeated for another portion of the target tissue region 42. Alternatively, the acoustic beam 15 may be steered continuously or discretely without any cooling time, e.g., using a mechanical positioner or electronic steering.

Figure 5:
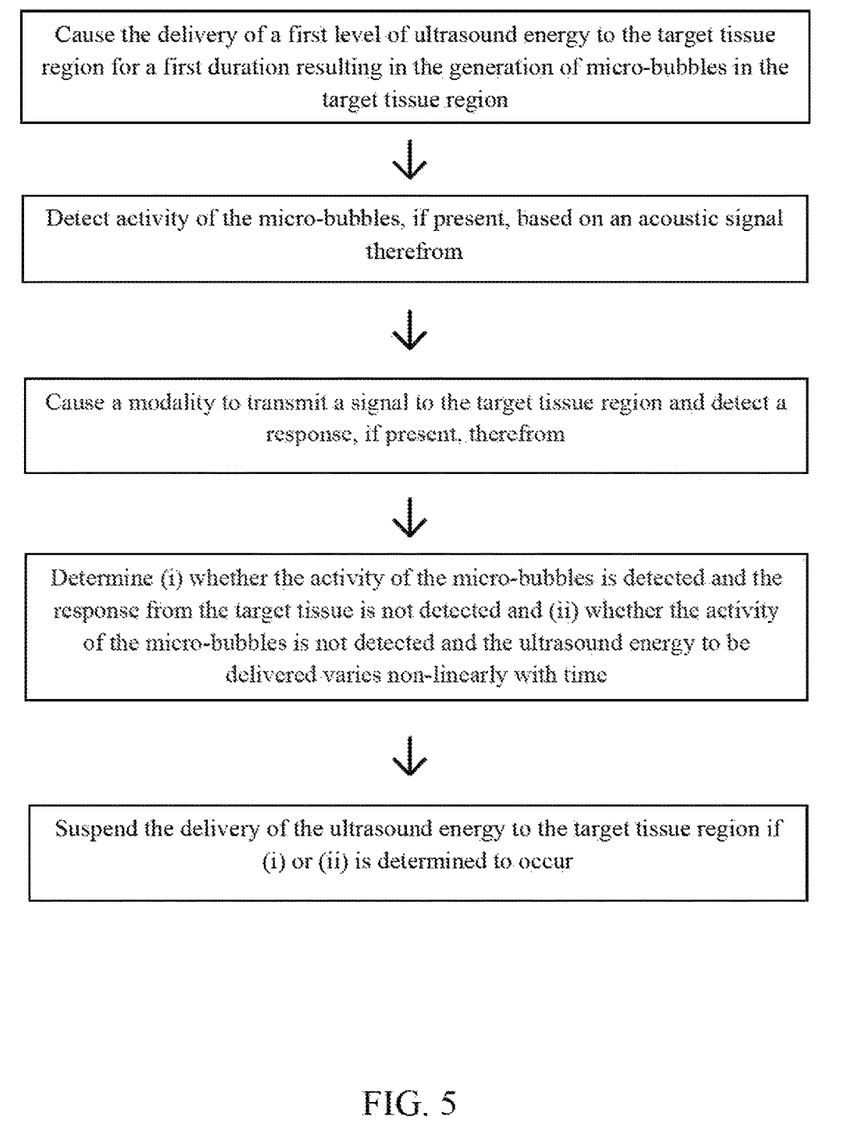
FIG. 5 is a flow chart illustrating an approach for delivering ultrasound energy to generate thermal energy in a target tissue region in a patient's body in accordance with various embodiments.

Referring to FIG. 5, in accordance with a more particular aspect of the invention, the controller 18 is preferably configured to cause the delivery of a first level of ultrasound energy to the target tissue region for a first duration resulting in the generation of micro-bubbles in the target tissue region; determine one or more characteristics of the target tissue region in the presence of the microbubbles; and cause the delivery of a second level of ultrasound energy from the transducer 14 to the target tissue region for a second duration, wherein one or both of the second ultrasound energy level and the second duration are based, at least in part, on the determined one or more characteristics of the target tissue 42 in the presence of the micro-bubbles.

By way of non-limiting examples, the characteristics may include one or more of a depth of the micro-bubbles from the patient's skin surface, tissue temperature, thermal dose profile, focal boundary, and intensity and/or density and/or three-dimensional locations of the micro-bubbles derived from images of the target tissue 42 in the presence of the micro-bubbles generated by the first level of ultrasound energy. Based on these characteristics, the second energy level may be determined by the controller 18 by adjusting one or more of a frequency, a phase, and an amplitude of a drive signal used to generate the second energy level in order to achieve a maximum coagulation volume while controlling a coagulation location and/or intensity. The second level of ultrasound energy may be delivered to the same or a different focal location in the target tissue 42 as the first level. By way of non-limiting example, the second level of ultrasound energy may be based, at least in part, on maintaining a temperature of the target tissue region 42 above, at, or below a prescribed threshold temperature.

By way of non-limiting example, the controller 18 may determine the one or more characteristics of the target tissue region based at least in part on temperature sensitive images of the target tissue region provided from the imager 20. Alternatively or additionally, the controller 18 may determine the one or more characteristics of the target tissue region, at least in part, based on an acoustic signal from the imploding micro-bubbles received by some of the transducer elements that are defined as receiver elements (it could be designed that all transducer elements will act as receivers) by the controller upon transmitting the first energy level. In particular, the signal generated by imploding micro-bubbles has a specific spectral signature, a peak at 0.5 f where f is the acoustic beam central frequency with white noise around it, so displaying the spectrum of the received signal will identify the presence of the micro-bubbles.

In essence, the detected acoustic signal and the MR images provide two independent feedback mechanisms for the controller 18. The MR images capture the effect of tissue heating generated by the non-linear event (the first level of energy), as well as the appearance of micro-bubbles when the density is above some threshold, since air micro-bubbles have no signal in MR. These two feedback mechanisms are used to identify situations in which the acoustic signal(s) detect micro-bubble activity, while the MR signal is not detecting any heating at the focus, or the acoustic signal(s) are not detecting any micro-bubble activity. In the case that micro-bubble activity is detect acoustically and no MR thermal signal is detected at the target, then there may be a situation of non-linear effect at some acoustic interface in the beam path. In this case, the system operator may be requested to stop the sonication to review the images for any unplanned heating. Alternatively, the controller 18 may do this automatically. If the acoustic signal is not detecting micro-bubbles activity and the sonication was planned to be non linear, the controller 18, or the system operator, may decide to stop sonication since the focus in non linear sonication is planned to be shifted to compensate for the non linear effect that is shifting the focus towards the transducer 14. The information extracted by the controller 18 from the transmission of the first energy level, like heating location, tissue temperature, and the existence of micro-bubbles, may be used to optimize the effect of the second energy level transmission by changing location of the second level (which may be done by changing the phase map of the transducer elements), changing the power level, frequency, etc.

The controller 18 may use a combination of temperature sensitive images and detected acoustic signals from the micro-bubbles to determine the second ultrasound energy level, as well as other parameters (e.g., duration, phase, frequency, location). By way of further non-limiting examples, the one or more characteristics of the target tissue region may be determined, at least in part, by obtaining an actual thermal dose distribution associated with the target tissue region in the presence of the micro-bubbles, and comparing the obtained actual thermal dose distribution with a predicted thermal dose distribution. Further, the controller may be configured to repeat the processes of determining one or more characteristics of the target tissue region in the presence of micro-bubbles in the target tissue region, and delivering the second level of ultrasound energy to the target tissue region, until a desired effect on the target tissue region is achieved.

As illustrated in the above embodiments, the imager 20 and the processor 22 provide feedback control to thereby allow the target tissue 42 to be treated efficiently and accurately using micro-bubbles, while protecting adjacent tissue desired to be protected. By using the imager 20 and the processor 22 to provide data on treatment location and damage volume, the system 10 or a user can control an ultrasound treatment that uses micro-bubbles, to thereby prevent, or at least reduce the risk of, irreversible tissue damage in non-targeted tissue.

The invention claimed is:

1. A focused ultrasound system, comprising:
   a transducer configured for delivering ultrasound energy to generate thermal energy in a target tissue region in a patient's body, and
   a controller configured for controlling a power, duration, frequency and focal location of the transducer, wherein the controller is further configured to:
   cause the delivery of a first level of ultrasound energy to the target tissue region for a first duration resulting in the generation of micro-bubbles in the target tissue region,
   detect activity of the micro-bubbles, if present, based on an acoustic signal therefrom,
   cause a modality to transmit a signal to the target tissue region and detect a response, if present, therefrom,
   determine (i) whether the activity of the micro-bubbles is detected and the response from the target tissue is not detected and (ii) whether the activity of the micro-bubbles is not detected and the ultrasound energy to be delivered varies non-linearly with time, and
   suspend the delivery of the ultrasound energy to the target tissue region if (i) or (ii) is determined to occur.

2. The system of claim 1, wherein the controller is further configured to:
   determine one or more characteristics of the target tissue region based at least in part on the response therefrom; and
   based on the determined one or more characteristics, cause delivery of a second level of ultrasound energy to the target tissue region for a second duration.

3. The system of claim 2, wherein the determined one or more characteristics of the target tissue region consist of one or more of:
   depth of the micro-bubbles from a skin surface of the patient,
   tissue temperature,
   thermal dose profile, and
   focal boundary.

4. The system of claim 3, wherein the controller is further configured to utilize a combination of temperature sensitive images provided by the modality and the acoustic signal to determine one or more of a frequency, a phase, a location, and an amplitude associated with the second level of ultrasound energy.

5. The system of claim 3, wherein the controller is further configured to deliver the second level of ultrasound energy to a different focal location in the target tissue region than the first level.

6. The system of claim 3, wherein the determination of the second level of ultrasound energy is based, at least in part, on maintaining a temperature of the target tissue region above a prescribed threshold temperature.

7. The system of claim 3, wherein the determination of the second level of ultrasound energy is based, at least in part, on maintaining a temperature of the target tissue region below a prescribed threshold temperature.

8. The system of claim 2, wherein the controller is further configured to determine the one or more characteristics of the target tissue region based, at least in part, on temperature sensitive images of the target tissue region provided from the modality.

9. The system of claim 1, wherein the modality comprises an imager configured for providing temperature sensitive images of the target tissue region illustrating an actual thermal dose distribution in the target tissue region based on the response therefrom.

10. The system of claim 9, wherein the controller is further configured to:
    utilize a combination of the temperature sensitive images and the acoustic signal to determine a second level of ultrasound energy to be delivered to the target tissue region; and
    cause delivery of the second level of ultrasound energy to the target tissue region.

11. The system of claim 10, wherein the controller is further configured to utilize the combination of the temperature sensitive images and the acoustic signal to determine one or more of a frequency, a phase, a duration, a location, and an amplitude associated with the second level of ultrasound energy.

12. The system of claim 10, wherein the controller is further configured to deliver the second level of ultrasound energy to a different focal location in the target tissue region than the first level.

13. The system of claim 10, wherein the determination of the second level of ultrasound energy is based, at least in part, on maintaining a temperature of the target tissue region above a prescribed threshold temperature.

14. The system of claim 10, wherein the determination of the second level of ultrasound energy is based, at least in part, on maintaining a temperature of the target tissue region below a prescribed threshold temperature.

15. The system of claim 10, wherein the second level of ultrasound energy is different from the first level of ultrasound energy.

16. The system of claim 10, wherein the controller is further configured to repeat processes of determining one or more characteristics of the target tissue region and delivering the second level of ultrasound energy to the target tissue region, until a desired effect on the target tissue region is achieved.

17. The system of claim 9, wherein the controller is further configured to:
- determine one or more characteristics of the target tissue region based, at least in part, on a comparison of the actual thermal dose distribution with a predicted thermal dose distribution; and
- based on the determined one or more characteristics of the target tissue region, cause delivery of a second level of ultrasound energy to the target tissue region for a second duration.

* * * * *